US011254765B2

(12) United States Patent
Chen et al.

(10) Patent No.: US 11,254,765 B2
(45) Date of Patent: Feb. 22, 2022

(54) POLYMERS OF HALOALKYL AND HALOALKENYL ETHER (METH)ACRYLATES

(71) Applicant: Arkema Inc., King of Prussia, PA (US)

(72) Inventors: Benjamin Bin Chen, Wayne, PA (US); Craig Alan Polsz, Newtown, PA (US); Lucy Clarkson, Chadds Ford, PA (US); Jing-Han Wang, King of Prussia, PA (US)

(73) Assignee: Arkema Inc., King of Prussia, PA (US)

( * ) Notice: Subject to any disclaimer, the term of this patent is extended or adjusted under 35 U.S.C. 154(b) by 0 days.

(21) Appl. No.: 16/651,399

(22) PCT Filed: Sep. 25, 2018

(86) PCT No.: PCT/US2018/052572
§ 371 (c)(1),
(2) Date: Mar. 27, 2020

(87) PCT Pub. No.: WO2019/067408
PCT Pub. Date: Apr. 4, 2019

(65) Prior Publication Data
US 2020/0299442 A1     Sep. 24, 2020

Related U.S. Application Data

(60) Provisional application No. 62/563,753, filed on Sep. 27, 2017.

(51) Int. Cl.
*C08F 220/14* (2006.01)
*C09D 133/16* (2006.01)
*C08F 220/22* (2006.01)
*C08F 220/24* (2006.01)

(52) U.S. Cl.
CPC .......... *C08F 220/24* (2013.01); *C08F 220/14* (2013.01); *C08F 220/22* (2013.01); *C09D 133/16* (2013.01)

(58) Field of Classification Search
CPC combination set(s) only.
See application file for complete search history.

(56) References Cited

U.S. PATENT DOCUMENTS

| | | | |
|---|---|---|---|
| 3,514,487 A | 5/1970 | Anello et al. | |
| 4,039,735 A | 8/1977 | Hrabak et al. | |
| 4,080,507 A * | 3/1978 | Gresham | C08F 20/28 560/223 |
| 5,026,902 A * | 6/1991 | Fock | C07C 69/653 560/223 |
| 5,045,397 A * | 9/1991 | Jensen | B32B 17/10045 428/429 |
| 5,302,678 A * | 4/1994 | Nomura | C08F 220/28 351/159.33 |
| 5,565,607 A * | 10/1996 | Maekawa | C07C 69/653 560/223 |
| 2017/0101556 A1* | 4/2017 | Keite-Telgenbuscher | H01L 23/293 |

FOREIGN PATENT DOCUMENTS

| | | | |
|---|---|---|---|
| CN | 104311756 A | 1/2015 | |
| CN | 104311756 A | 1/2015 | |
| JP | 01305052 A * | 12/1989 | |
| JP | 0497117 A | 3/1992 | |
| WO | WO-2015154947 A1 * | 10/2015 | H01L 51/004 |

OTHER PUBLICATIONS

Liu, "Artificial neural network prediction of glass transition temperature of polymers", Colloid Polym Sci. (2009) 287, 811-818 (Year: 2009).*

Journal of Fluorine Chemistry—Convenient Synthesis of 3,3,3 Trifluoropropanoic Acid by Hydrolytic Oxidation of 3,3,3,-Trifluorpropanal Dimethyl Acetal; Takeo Komata et al Journal of Flourine 129 (2008) 35-39.

A Novel & Convenient Synthesis of (Z)-3,3,3-Trufluoroproenyl Alkyl Ethers & CF3-Substituted Propyl Acetals as Versatile CF3-Containg Building Blocks Chem Comm 1996; Feng Hong et al—Shanghai Inst of Organic Chemisty pp. 57-58.

Shin-Ichi Chikada, et al; "Synthesis and Polymerization of Novel Macromonomers with Fluorine Containing Poly (ethylene glycol)"; Japanese Journal of Polymer Science and Technology; vol. 68, No. 4, Jan. 1, 2011, pp. 190-194.

* cited by examiner

*Primary Examiner* — Nicole M. Buie-Hatcher
(74) *Attorney, Agent, or Firm* — Steven D. Boyd

(57) ABSTRACT

A curable composition containing at least one of a haloalkyl ether (meth)acrylate or a haloalkenyl ether (meth)acrylate and, optionally, one or more different types of co-monomers is cured to provide a polymer having advantageous properties as a result of the incorporation of halogenated functionality derived from the haloalkyl/haloalkenyl ether (meth) acrylate monomer.

14 Claims, No Drawings

POLYMERS OF HALOALKYL AND HALOALKENYL ETHER (METH)ACRYLATES

This present application is the national phase under 35 USC § 371 of prior PCT International Application Number PCT/US2018/052572 filed Sep. 25, 2018 which designated the United States of America and claimed priority to U.S. Provisional Patent Application Ser. No. 62/563,753 filed Sep. 27, 2017.

FIELD OF THE INVENTION

The invention relates to polymers of haloalkyl/haloalkenyl ether (meth)acrylates (including copolymers of haloalkyl/haloalkenyl ether (meth)acrylates with other (meth)acrylate-functionalized compounds), methods for making such polymers, curable compositions useful for preparing such polymers, and products comprising such polymers.

BACKGROUND OF THE INVENTION

Halogenated polymers and copolymers have long been of commercial interest due to their generally superior weatherability, chemical resistance, and electrochemical stability as compared to non-halogenated analogous polymers and copolymers.

One example is fluoropolymer-based coatings and films, which are widely used because of their outstanding properties. Often, these coatings and films are based not on fluoroolefin homopolymers, such as PVDF or PCTFE, but rather on copolymers containing two or more monomers (at least one of which is fluorinated). Illustrative copolymers of this type include copolymers of VF2 such as those described in U.S. Pat. No. 5,925,705 and PCT Application Publication WO 9810000, U.S. Pat. No. 5,093,427 and PCT Application Publication WO 98/38242, copolymers of TFE including ETFE, and copolymers of CTFE or TFE with vinyl ethers, vinyl esters, or allyl ethers or esters. In coating applications, these copolymers may additionally be blended with non-fluorinated co-resins; for example, coatings and films based on blends of VF2 homopolymer or copolymer, along with miscible acrylic resins, are well known for their outstanding outdoor weatherability properties, as well as other properties such as chemical resistance and formability.

Other classes of halogenated copolymers which are used in coatings are the so-called FEVE copolymers, which are alternating copolymers of CTFE or TFE with non-halogenated vinyl ethers, and the so-called fluoroacrylics, which are copolymers of (meth)acrylate monomers containing some degree of fluorination on their pendant side chains. FEVE copolymers are known for very good weatherability, high gloss, and their ease of use with various crosslinking chemistries. Fluoroacrylics are also commonly crosslinked and are well known for their anti-graffiti and stain resistance properties.

Notwithstanding the halogenated polymers and copolymers known in the art, it would be desirable to develop new halogenated polymers and copolymers which have different or improved characteristics and properties.

BRIEF SUMMARY OF THE INVENTION

The present invention provides a polymer comprising, in polymerized form, at least one of a haloalkyl ether (meth)acrylate comprising a haloalkyl moiety bonded through an ether linkage and an organic spacer moiety to a (meth)acrylate functional group or a haloalkenyl ether (meth)acrylate comprising a haloalkenyl moiety bonded through an ether linkage and an organic spacer moiety to a (meth)acrylate functional group. In further embodiments of the invention, an allyl functional group may be substituted for the (meth)acrylate functional group.

The haloalkyl ether (meth)acrylate may, for example, correspond to general structure (I):

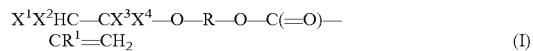

wherein R is an organic moiety, $X^1$, $X^2$, $X^3$ and $X^4$ are independently selected from hydrogen, halogen or haloalkyl, subject to the proviso that at least one of $X^1$, $X^2$, $X^3$ or $X^4$ is halogen or a haloalkyl group, and $R^1$ is hydrogen or methyl.

The haloalkenyl ether (meth)acrylate may, for example, correspond to general structure (IA):

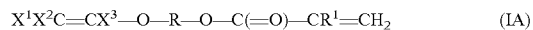

wherein R is an organic moiety, $X^1$, $X^2$ and $X^3$ are independently selected from hydrogen, halogen or haloalkyl, subject to the proviso that at least one of $X^1$, $X^2$ or $X^3$ is halogen or a haloalkyl group, and $R^1$ is hydrogen or methyl.

The haloalkyl ether (meth)acrylate(s) and/or haloalkenyl ether (meth)acrylates may be copolymerized with one or more other types of monomers, including in particular ethylenically unsaturated comonomers such as (meth)acrylate-functionalized compounds other than haloalkyl ether (meth)acrylates and haloalkenyl ether methacrylates. The polymers of the present invention may be prepared by polymerization (curing) of curable compositions comprising a) at least one of i) a haloalkyl ether (meth)acrylate comprising a haloalkyl moiety bonded through an ether linkage and an organic spacer moiety to a (meth)acrylate functional group or ii) a haloalkenyl ether (meth)acrylate comprising a haloalkenyl moiety bonded through an ether linkage and an organic spacer moiety to a (meth)acrylate functional group and, optionally, b) at least one of iii) a (meth)acrylate-functionalized compound other than a haloalkyl ether (meth)acrylate comprising a haloalkyl moiety bonded through an ether linkage and an organic spacer moiety to a (meth)acrylate functional group or a haloalkenyl ether (meth)acrylate comprising a haloalkenyl moiety bonded through an ether linkage and an organic spacer moiety to a (meth)acrylate functional group or iv) a curing agent.

DETAILED DESCRIPTION OF CERTAIN EMBODIMENTS OF THE INVENTION

The polymers of the present invention comprise, in polymerized form, at least one haloalkyl/haloalkenyl ether (meth)acrylate and, optionally, at least one co-monomer capable of copolymerizing with the haloalkyl/haloalkenyl ether (meth)acrylate(s), wherein the particular haloalkyl/haloalkenyl ether (meth)acrylate(s) and optional co-monomer(s) may be selected so as to impart desirable or improved properties to the polymer obtained by polymerization of such monomers. It is, therefore, an object of this invention to provide improved curable compositions and polymeric compositions, preferably for coating, film, fiber (textile) and sheet applications. It is another object of this invention to provide polymeric compositions having improved mechanical and physical properties as well as curable (polymerizable) compositions useful for producing such polymeric compositions. It is a further object of this invention to provide polymeric compositions which are highly resistant to abrasion, scratch, wear, staining, fouling and corrosion and to attack by chemicals and the like, as well as curable compositions capable of being cured (polymerized) to yield such polymeric compositions. It is still another object to provide improved polymeric compositions which are capable of shedding off dirt, grease, finger prints and the like. It is a still further object of this invention to provide polymeric compositions having improved UV resistance, or weatherability. Other objects of this invention are to provide a method for preparing polymeric compositions having improved properties and to provide a curable composition useful for making such polymeric compositions.

Haloalkyl Ether (Meth)acrylates and Haloalkenyl Ether (Meth)acrylates

Haloalkyl ether (meth)acrylates useful in the present invention may be characterized as organic compounds which comprise a haloalkyl moiety bonded through an ether linkage and an organic spacer moiety (in that sequence) to a (meth)acrylate functional group. Haloalkenyl ether (meth)acrylates useful in the present invention may be characterized as organic compounds which comprise a haloalkenyl moiety bonded through an ether linkage and an organic spacer moiety (in that sequence) to a (meth)acrylate functional group. Haloalkyl ether (meth)acrylates and haloalkenyl ether (meth)acrylates may sometimes be collectively referred to herein as "haloalkyl/haloalkenyl ether (meth)acrylates". As used herein, the term "(meth)acrylate" refers to acrylate ($-C(=O)CH=CH_2$) and methacrylate ($-C(=O)C(CH_3)=CH_2$) functional groups. As used herein, the term "haloalkyl" refers to an alkyl group which is substituted with one or more halogen atoms, which may be the same as or different from each other if more than one halogen atom is present. As used herein, the term "haloalkenyl" refers to an alkenyl group which is substituted with one or more halogen atoms, which may be the same as or different from each other if more than one halogen atom is present. Where the haloalkyl or haloalkenyl group contains two or more carbon atoms, halogen(s) may be substituted on any or all of the carbon atoms. An individual carbon atom in the haloalkyl or haloalkenyl group may be substituted with one, two or three halogen atoms, which may be the same as or different from each other. In addition to halogen, individual carbon atoms within the haloalkyl or haloalkenyl group may be substituted with one or more hydrogen atoms. Where the haloalkyl or haloalkenyl group contains two or more carbon atoms, one or more carbon atoms may be non-halogenated, provided that at least one carbon atom is halogenated. As used herein, the term "alkyl" means a paraffinic hydrocarbon group which may be derived from an alkane by dropping one hydrogen from the formula, such as ethyl ($CH_3CH_2-$). As used herein, the term "alkenyl" refers to an unsaturated hydrocarbon group having at least one carbon-carbon double bond which may be derived from an alkene by dropping one hydrogen from the formula, such as propenyl ($CH_3CH=CH-$ or $CH_2=C(CH_3)-$). The term halogen, as used herein, means fluorine (F), chlorine (Cl), bromine (Br) or iodine (I).

In certain embodiments, the haloalkyl ether (meth)acrylate corresponds to general structure (I)

$$X^1X^2HC-CX^3X^4-O-R-O-C(=O)-CR^1=CH_2 \quad (I)$$

wherein R is an organic moiety, $X^1$, $X^2$, $X^3$ and $X^4$ are independently selected from hydrogen, halogen or haloalkyl, subject to the proviso that at least one of $X^1$, $X^2$, $X^3$ or $X^4$ is halogen or a haloalkyl group, and $R^1$ is hydrogen or methyl. According to certain embodiments of the invention, at least two of $X^1$, $X^2$, $X^3$ or $X^4$ are selected from the group consisting of halogens and haloalkyl groups. At least two of $X^1$, $X^2$, $X^3$ or $X^4$ are selected from the group consisting of fluorine and fluoroalkyl groups, in certain embodiments. In other embodiments, at least one of $X^1$, $X^2$, $X^3$ or $X^4$ is fluorine or a fluoroalkyl group. Each of $X^1$, $X^2$, $X^3$ and $X^4$ is halogen or a haloalkyl group, according to other embodiments of the invention. One of $X^1$, $X^2$, $X^3$ or $X^4$ may be a C1-C8 haloalkyl group, in particular a C1-C8 fluoroalkyl group such as a C1-C8 perfluoroalkyl group (e.g., trifluoromethyl).

In other embodiments, the haloalkenyl ether (meth)acrylate corresponds to general structure (IA)

$$X^1X^2C=CX^3-O-R-O-C(=O)-CR^1=CH_2 \quad (IA)$$

wherein R is an organic moiety, $X^1$, $X^2$ and $X^3$ are independently selected from hydrogen, halogen or haloalkyl, subject to the proviso that at least one of $X^1$, $X^2$ or $X^3$ is halogen or a haloalkyl group, and $R^1$ is hydrogen or methyl. According to certain embodiments of the invention, at least two of $X^1$, $X^2$ or $X^3$ are selected from the group consisting of halogens and haloalkyl groups. At least two of $X^1$, $X^2$ or $X^3$ are selected from the group consisting of fluorine and fluoroalkyl groups, in certain embodiments. In other embodiments, at least one of $X^1$, $X^2$ or $X^3$ is fluorine or a fluoroalkyl group. Each of $X^1$, $X^2$ and $X^3$ is halogen or a haloalkyl group, according to other embodiments of the invention. One of $X^1$, $X^2$ or $X^3$ may be a C1-C8 haloalkyl group, in particular a C1-C8 fluoroalkyl group such as a C1-C8 perfluoroalkyl group (e.g., trifluoromethyl).

Illustrative examples of suitable haloalkyl ether moieties include, without limitation:

$CH_3-CF_2-O-$ $CH_3-CFH-O-$ $CH_2F-CF_2-O-$ $CF_3CF(CH_3)-O-$ $CF_2H-CF_2-O-$ $CH_2Cl-CF_2-O-$ $CH_3C(CF_3)Cl-O-$ $CH_2Cl-CH(CF_3)-O-$ $CFH_2-CF(CF_3)-O-$ $CF_3CH_2-CF_2-O-$ $CF_3CFH-CF_2-O-$ $CH_3-CF(CH_2CF_3)-O-$ $CF_3-CH_2-CF(CH_3)-O-$ $CF_3-CH_2-CF(CF_3)-O-$ $CF_3-CH_2-CCl(CF_3)-O-$ $CH_3CF(CH_2CF_2H)-O-$ $CH_2Cl-CF(CH_2CF_2H)-O-$ $CF_2H-CH_2-CF(CH_2Cl)-O-$ $CH_3CHCl-O-$ $CH_2Cl-CHCl-O-$ $CH_3CCl_2-O-$ $CFClH-CF_2-O-$ $CH_3-CCl(CF_3)-O-$ $CClH_2-CCl(CF_3)-O-$ $CF_3-CH_2-CCl_2-O-$ $CCl_2H-CF(CF_3)-O-$ $CFClH-CF(CF_3)-O-$ $CClH_2-CF(CF_3)-O-$ $CFH_2-CCl(CF_3)-O-$ $CF_3-CHCl-CF_2-O-$ $CF_3-CHCl-CFCl-O-$

Illustrative examples of suitable haloalkenyl ether moieties include, without limitation, moieties analogous to the above-mentioned haloalkyl ether moieties, but where hydrohalide has been eliminated to form a carbon-carbon double bond between the carbon bonded to the ether oxygen and the adjacent carbon atom.

In certain embodiments of the invention, the polymer comprises, in polymerized form, at least one haloalkyl ether (meth)acrylate corresponding to general structure (I) wherein a) $X^1$ is chlorine and $X^2$, $X^3$ and $X^4$ are fluorine or b) $X^3$ is chlorine and $X^1$, $X^2$ and $X^4$ are fluorine. R may be an alkylene segment or a poly(oxyalkylene) segment, in certain aspects of the invention. As used herein, the term "alkylene" means a paraffinic hydrocarbon group which may be derived from an alkane by dropping two hydrogens from the formula, such as ethylene ($-CH_2CH_2-$), propylene ($-CH_2CH(CH_3)-$). The term "oxyalkylene" means an alkylene group coupled to an ether oxygen, as in oxyethylene for example ($-CH_2CH_2O-$), oxypropylene for example ($-CH_2CH(CH_3)O-$). Thus, in various aspects of the invention, the polymer comprises, in polymerized form, at least one haloalkyl/haloalkenyl ether (meth)acrylate corresponding to general structure (I) or (IA) wherein R is an ethylene segment or a poly(oxyethylene) segment. For example, R may be $-[CH_2CH_2O]_n-CH_2CH_2-$ wherein n is 0 or an integer of from 1 to 10 or higher. Although R may be a substituted or heteroatom-containing organic moiety, such as an oxygen-containing organic moiety, in certain embodiments R is non-halogenated (i.e., does not contain any halogen atoms). R may be, for example, aliphatic (including straight chain or branched aliphatic or cycloaliphatic), aromatic, or contain both aliphatic and aromatic structural units, but in certain embodiments is aliphatic and does not contain any aromatic structural units. In particular, R may be a saturated aliphatic organic moiety, optionally containing one or more oxygen atoms such as ether oxygen atoms (oxygen atoms forming an ether linkage).

The moiety $X^1X^2HC-CX^3X^4-O-R-O-$ or $X^1X^2C=CX^3-O-R-O-$, according to certain embodiments, may have a molecular weight not greater than 900 daltons, not greater than 800 daltons or not greater than 700 daltons.

Mixtures of two or more different haloalkyl/haloalkenyl ether (meth)acrylates may be used to prepare polymers in accordance with the present invention.

In various embodiments of the invention, the haloalkyl/haloalkenyl ether (meth)acrylate used to prepare the polymer may have a purity (as calculated in weight percent) of at least 80, at least 85, at least 90, at least 95, at least 99, at least 99.9 or even 100%.

Methods of Making Haloalkyl Ether (Meth)Acrylates and Haloalkenyl Ether (Meth)Acrylates Although any suitable methods may be used to synthesize and purify haloalkyl/alkenyl ether (meth)acrylates suitable for polymerization to provide polymers in accordance with the present invention, the particular procedures described in the United States Provisional Application being filed simultaneously herewith under U.S. application Ser. No. 62/563,736 may be utilized. The disclosure of the aforementioned Provisional Application is incorporated herein by reference in its entirety for all purposes.

For example, suitable haloalkyl/haloalkenyl ether (meth)acrylates may be prepared by any of the following methods:

Method A: Reaction of a hydroxyl-functionalized (meth)acrylate with a halogenated olefin containing a carbon-carbon double bond, wherein at least one carbon of the carbon-carbon double bond is substituted with at least one of halogen or a haloalkyl group (in particular, a fluoroalkyl group such as a perfluoroalkyl group, e.g., trifluoromethyl), to produce the haloalkyl/haloalkenyl ether (meth)acrylate.

Method B: Reaction of a polyol (e.g., a diol) with a halogenated olefin under conditions effective to favor reaction of the halogenated olefin at fewer than all of the hydroxyl groups of the polyol (e.g., at just one of the two hydroxyl groups of a diol), yielding a haloalkyl ether or haloalkenyl ether of the polyol containing one or more unreacted hydroxyl groups. For example, where the polyol is a diol, a monohaloalkyl or monoalkenyl ether of the diol is formed, the remaining hydroxyl group of which is reacted to form a (meth)acrylate group.

Method C: Reaction of a halogenated olefin with a polyol (e.g., a diol) in which fewer than all of the hydroxyl groups of the polyol have been blocked or masked (herein sometimes referred to as a "partially masked polyol" or "partially masked diol" where the polyol is a diol), yielding an intermediate in which one or more of the free hydroxyl group(s) of the partially masked polyol has or have been converted to a haloalkyl ether or haloalkenyl ether group. The blocked/masked hydroxyl(s) group of the intermediate is or are deprotected, then reacted to form a (meth)acrylate group.

If it is desired to produce a haloalkyl ether (meth)acrylate rather than a haloalkenyl ether (meth)acrylate, the reaction involving the halogenated olefin and further processing conditions should be selected so as to reduce the amount of elimination exhibited by the reaction product, which would lead to the production of an alkenyl ether group rather than the desired haloalkyl ether functionality. Conversely, if a haloalkenyl ether (meth)acrylate product is desired, more basic reaction conditions can be used during the reaction involving the halogenated olefin so as to promote elimination.

The halogenated olefin may contain one, two, three, four or more halogen atoms (F, Cl, Br, and/or I) in particular one, two, three, four or more fluorine atoms. The halogenated olefin may have a fluorinated alkyl group substituted on one carbon of the carbon-carbon double bond. For example, the halogenated olefin may have a perfluorinated alkyl group substituted on one carbon of the carbon-carbon double bond.

According to certain embodiments, the halogenated olefin starting material may have a structure in accordance with formula (1):

wherein $X^1$, $X^2$, $X^3$ and $X^4$ are independently selected from the group consisting of hydrogen (H), chlorine (Cl), fluorine (F), bromine (Br), iodine (I) and halogenated and non-halogenated C1-C20 alkyl groups, subject to the proviso that one or more of $X^1$, $X^2$, $X^3$ and $X^4$ is selected from the group consisting of chlorine (Cl), fluorine (F), bromine (Br), iodine (I) and halogenated alkyl groups.

For example, the halogenated olefin may be selected from the group consisting of $CClF=CH_2$, $CH_2=CF_2$, $CFH=CH_2$, $CF_2=CHF$, $CF_3CF=CH_2$, $CF_2=CF_2$, $CH_2=CHCl$, $CHCl=CHCl$, $CH_2=CCl_2$, $CF_2=CFCl$; $CF_2=CHCl$, $CF_3CCl=CH_2$, $CF_3CCl=CClH$, $CF_3CH=CCl_2$, $CF_3CF=CCl_2$, $CF_3CF=CClH$, $CF_3CCl=CFH$, $CF_3CCl=CF_2$, $CF_3CCl=CFCl$, $CF_3CF=CFCl$, $CF_3CH=CHCl$, $CF_3CF=CFH$, $CF_3CH=CF_2$, $CF_3CF=CF_2$, $CF_3CH_2CF=CH_2$, $CF_3CH=CFCH_3$, $CF_3CF=CHCF_3$, $CF_3CCl=CHCF_3$, $CF_2HCH_2CF=CH_2$, $CF_2HCH_2CF=CHCl$ and $CF_2HCH=CFCH_2Cl$.

Other suitable fluorinated olefins are cyclo-fluorobutenes, cyclo-chlorofluorobutenes, cyclo-fluoropentenes, cyclo-chlorofluoropentenes, cyclo-fluorohaxenes, and cyclo-chlorofluorohaxenes, such as 1-chloro-2,3,3-trifluorocyclobutene, 1,2-dichlorotetrafluorocyclobutene, hexafluorocyclobutene, 1H-heptafluorocyclopentene, 1-chloro-3,3,4,4,5,5-hexafluorocyclopentene, 1-chloroheptafluorocyclopentene, octafluorocyclopentene, 1,2-dichlorohexafluorocyclopentene, 1,2,3-trichloropentafluorocyclopentene, perfluorocyclohexene, 1,2-dichlorooctafluorocyclohexene, 1H-perfouorocyclohexene, and the like.

The hydroxyl-functionalized (meth)acrylate used in Method A preferably is a hydroxyalkyl (meth)acrylate or an alkoxylated hydroxyalkyl (meth)acrylate, such as a hydroxyethyl (meth)acrylate, hydroxypropyl (meth)acrylate, ethoxylated hydroxyethyl (meth)acrylate or ethoxylated hydroxypropyl (meth)acrylate.

The polyol used in Method B preferably is an aliphatic diol or polyalkylene glycol. Suitable aliphatic diols include C2-C22 aliphatic diols (i.e., straight chain, branched and cyclic aliphatic compounds containing two to 22 carbon atoms and two hydroxyl groups per molecule, wherein the hydroxyl groups preferably are primary or secondary and may be substituted on any of the carbon atoms, including at the terminal positions of a hydrocarbon chain). Suitable polyalkylene glycols include oligomers and polymers of alkylene oxides such as ethylene oxide, propylene oxide, butane oxide, tetrahydrofuran and the like and combinations thereof, as well as alkoxylated products of aliphatic diols.

The partially masked polyol used in Method C preferably is a partially masked aliphatic diol or partially masked polyalkylene glycol. Suitable aliphatic diols and polyalkylene glycols include any of the above-mentioned aliphatic diols and polyalkylene glycols. Any of the types of hydroxyl masking groups known in the field of organic chemistry may be used to block one of the two hydroxyl groups of a diol to provide the partially masked diol. Typically, however, it will be desirable to employ a blocking or masking group that remains stable (i.e., is not removed to any significant extent) under the conditions used to react the masked diol with the halogenated olefin. For example, if a basic catalyst is employed during the masked diol/halogenated olefin reaction, the blocking/masking group(s) should be resistant to deblocking or demasking under such basic conditions. Illustrative examples of suitable blocking/masking groups include, but are not limited to, silyl ether groups, acetal groups, ketal groups, benzyl groups and the like. Other examples of suitable protecting groups for hydroxyl functional groups include, but are not limited to, acetyl (Ac), benzoyl (Bz), beta-methoxyethoxymethylether (MEM), dimethoxytrityl (DMT), methoxymethyl ether (MOM), methoxytrityl (MMT), p-methoxybenzyl ether (PMB), methylthiomethyl ether, pivaloyl (Piv), tetrahydropyranyl (THP), tetrahydrofuryl (THF), trityl (triphenylmethyl, Tr), silyl ether, methyl ether, t-butyl ether and ethoxyethyl ether (EE). Once the partially masked diol has been reacted with the halogenated olefin to yield an intermediate containing a haloalkyl ether or haloalkenyl group and a masked hydroxyl group, the masked hydroxyl group may then be deprotected using any of the suitable procedures known in the field of organic chemistry and the resulting free hydroxyl group esterified with a reactant capable of introducing a (meth)acrylate functional group (e.g., (meth)acrylic acid, (meth)acrylic anhydride, (meth)acryloyl halide or a C1-C4 alkyl ester of (meth)acrylic acid) to produce the desired haloalkyl/haloalkenyl ether (meth)acrylate.

The reaction of the halogenated olefin with the hydroxyl-functionalized (meth)acrylate, diol or partially masked diol may be carried out under basic conditions, for example in the presence of an inorganic base such as an alkali metal hydroxide or an alkali metal salt of carbonic acid (e.g., sodium carbonate). Such reaction may be carried out in a liquid medium, for example a liquid medium comprised of one or more organic solvents such as a polar, non-protic organic solvent. A phase transfer catalyst may be present during the reaction.

The hydroxyl-functionalized (meth)acrylate (or polyol or partially masked polyol) and the halogenated olefin may be reacted at a temperature of from about 25° C. to about 200° C. (e.g., from about 25° C. to about 120° C.) for a time of from about 0.5 hours to about 24 hours. The hydroxyl-functionalized (meth)acrylate (or polyol or partially masked polyol) and the halogenated olefin may be reacted in a stoichiometric ratio of (moles hydroxyl-functionalized (meth)acrylate, polyol or partially masked polyol)/x:moles halogenated olefin, wherein x=number of active hydrogens per molecule of the hydroxyl-functionalized (meth)acrylate (or polyol or partially masked polyol)), of from about 1:8 to about 8:1. In the case of Method B, it is generally preferred to use a stoichiometric excess of polyol to halogenated olefin so as to favor the production of a reaction product where fewer than all of hydroxyl groups have reacted with halogenated olefin. Production of such a reaction product may also be favored, for example, by using a polyol containing at least one primary hydroxyl group and at least one secondary hydroxyl group, whereby the primary hydroxyl group(s) react(s) preferentially with the halogenated olefin.

In the case of Methods B and C, the desired (meth)acrylate functional group may be introduced by reacting the free hydroxyl group with a suitable reagent such as (meth)acrylic acid, (meth)acryloyl halide, (meth)acrylic anhydride or a short chain (C1-C4) alkyl (meth)acrylate in an esterification reaction.

As previously mentioned, the haloalkyl/haloalkenyl ether (meth)acrylate may be prepared using a halogenated olefin (for example, a fluorinated olefin) as a reactant. As used herein, the term "halogenated olefin" refers to an organic compound containing at least one carbon-carbon double bond and at least one halogen atom (Cl, F, Br, I). As used herein, the term "fluorinated olefin" refers to an organic compound containing at least one carbon-carbon double bond and at least one fluorine atom (and optionally one or more halogen atoms other than fluorine).

The halogenated olefin may contain one, two, three or more halogen atoms, such as bromine, chlorine, fluorine or iodine atoms or combinations thereof (e.g., at least one fluorine atom and at least one chlorine atom). In certain embodiments, the halogenated olefin contains at least one halogen atom substituted on at least one of the carbon atoms involved in a carbon-carbon double bond present in the halogenated olefin. Suitable fluorinated olefins include olefins containing one, two, three or more fluorine (F) atoms. The fluorine atom(s) may be substituted on one or both of the carbon atoms involved in a carbon-carbon double bond and/or may be present as a substituent on a moiety, such as an alkyl group, that is attached to one or both of the carbon atoms involved in a carbon-carbon double bond. For example, the fluorinated olefin may comprise one or more fluoroalkyl (e.g., perfluoroalkyl) groups, such as fluoromethyl, difluoromethyl, trifluoromethyl, fluoroethyl, difluoroethyl, trifluoroethyl, tetrafluoroethyl, perfluoroethyl, fluoropropyl, difluoropropyl, trifluoropropyl, tetrafluoropropyl, pentafluoropropyl, hexafluoropropyl, perfluoropropyl and the like and analogues thereof wherein wherein a portion of the fluorine atoms and/or one or more of the hydrogen atoms are replaced with other halogen atoms (e.g., Cl). The fluorinated olefin may comprise one or more halogen atoms other than fluorine, in particular one or more chlorine (Cl), iodine (I) and/or bromine (Br) atoms. In certain embodiments of the invention, the halogenated olefin or fluorinated olefin may comprise at least one chlorine atom substituted on a carbon atom involved in a carbon-carbon double bond. In further embodiments of the invention, the halogenated olefin or fluorinated olefin may comprise at least one hydrogen atom substituted on a carbon atom involved in a carbon-carbon double bond. For example, fluoroolefins, hydrofluoroolefins, chloroolefins, hydrochloroolefins, chlorofluoroolefins, and hydrochlorofluoroolefins may all be employed as the halogenated olefin reactant in the present invention. Suitable types of fluorinated olefins include fluoroethylenes, chlorofluoroethylenes, fluoropropenes, chlorofluoropropenes, fluorobutenes, chlorofluorobutenes, fluoropentenes, chlorofluoropentenes, fluorohexenes, chlorofluorohexenes and the like. In various embodiments of the invention, the halogenated olefin comprises two, three, four, five, six or more carbon atoms, e.g., 2-20 carbon atoms, 2-8 carbon atoms, 2-6 carbon atoms or 2-4 carbon atoms.

According to certain aspects, the halogenated olefin may have a structure in accordance with formula (1):

$$CX^1X^2=CX^3X^4 \qquad (1)$$

wherein $X^1$, $X^2$, $X^3$ and $X^4$ are independently selected from the group consisting of hydrogen (H), chlorine (Cl), fluorine (F), bromine (Br), iodine (I) and halogenated and non-halogenated C1-C20 alkyl groups, subject to the proviso that one or more of $X^1$, $X^2$, $X^3$ and $X^4$ is chlorine (Cl), fluorine (F), bromine (Br), iodine (I) or a halogenated alkyl group (e.g., a fluorinated alkyl group such as trifluoromethyl).

Specific representative examples of halogenated olefins suitable for use in preparing the haloalkyl/haloalkenyl ether (meth)acrylate include, but are not limited to:

$CClF=CH_2$ $CH_2=CF_2$ $CFH=CH_2$ $CF_2=CHF$ $CF_3CF=CH_2$ $CF_2=CF_2$ $CF_2=CHCl$ $CF_3CCl=CH_2$ $CF_3CH=CHCl$ $CF_3CF=CFH$ $CF_3CH=CF_2$ $CF_3CF=CF_2$ $CF_3CH_2CF=CH_2$ $CF_3CH=CFCH_3$ $CF_3CF=CHCF_3$ $CF_3CCl=CHCF_3$ $CF_2HCH_2CF=CH_2$ $CF_2HCH_2CF=CHCl$ $CF_2HCH=CFCH_2Cl$ $CH_2=CHCl$ $CHCl=CHCl$ $CH_2=CCl_2$ $CF_2=CFCl$;

$CF_3CCl=CH_2$ $CF_3CCl=CClH$ $CF_3CH=CCl_2$ $CF_3CF=CCl_2$ $CF_3CF=CFCl$ $CF_3CF=CClH$ $CF_3CCl=CFH$ $CF_3CCl=CF_2$ $CF_3CCl=CFCl$

All possible isomers (e.g., E or Z isomers) of the above-mentioned halogenated olefins can be used.

In one embodiment, a chloro-substituted trifluoropropenyl compound is employed as the halogenated olefin. Suitable chloro-substituted trifluoropropenyl compounds include 1-chloro-3,3,3-trifluoro-prop-1-ene (also known as 1233zd) and 2-chloro-3,3,3-trifluoroprop-1-ene. Either the cis or trans isomer of 1-chloro-3,3,3-trifluoro-prop-1-ene may be used (i.e., trans-(E)-1233zd or cis-(Z)-1233zd).

Other suitable fluorinated olefins are cyclo-fluorobutenes, cyclo-chlorofluorobutenes, cyclo-fluoropentenes, cyclo-chlorofluoropentenes, cyclo-fluorohaxenes, and cyclo-chlorofluorohaxenes, such as 1-chloro-2,3,3-trifluorocyclobutene, 1,2-dichlorotetrafluorocyclobutene, hexafluorocyclobutene, 1H-heptafluorocyclopentene, 1-chloro-3,3,4,4,5,5-hexafluorocyclopentene, 1-chloroheptafluorocyclopentene, octafluorocyclopentene, 1,2-dichlorohexafluorocyclopentene, 1,2,3-trichloropentafluorocyclopentene, perfluorocyclohexene, 1,2-dichlorooctafluorocyclohexene, 1H-perfouorocyclohexene, and the like.

Hydroxyl-functionalized (meth)acrylates suitable for use as the other reactant in Method A may be characterized as organic compounds containing both a hydroxyl (—OH) functional group and a (meth)acrylate functional group. Preferably, the hydroxyl is a primary or secondary aliphatic hydroxyl group, but in other embodiments could be phenolic.

According to certain embodiments, the hydroxyl-functionalized (meth)acrylate corresponds to structural formula (II):

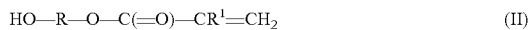

HO—R—O—C(=O)—CR$^1$=CH$_2$ (II)

wherein R is an organic moiety and R$^1$ is hydrogen or methyl, or fluorine or trifluoromethyl.

R may be an alkylene segment or a poly(oxyalkylene) segment, in certain aspects of the invention. As used herein, the term "alkylene" means a paraffinic hydrocarbon group which may be derived from an alkane by dropping two hydrogens from the formula, such as ethylene (—CH$_2$CH$_2$—). The term "oxyalkylene" means an alkylene group coupled to an ether oxygen, as in oxyethylene for example (—CH$_2$CH$_2$O—). Thus, in various aspects of the invention, the hydroxyl-functionalized (meth)acrylate used to react with the halogenated olefin corresponds to general structure (II) wherein R is an ethylene segment or a poly(oxyethylene) segment. For example, R may be —[CH$_2$CH$_2$O]$_n$—CH$_2$CH$_2$— wherein n is 0 or an integer of from 1 to 10 or 1 to 100 or higher. Although R may be a substituted or heteroatom-containing organic moiety, such as an oxygen-containing organic moiety, in certain embodiments R is non-halogenated (i.e., does not contain any halogen atoms). R may be, for example, aliphatic (including straight chain or branched aliphatic or cycloaliphatic), aromatic, or contain both aliphatic and aromatic structural units, but in certain embodiments is aliphatic and does not contain any aromatic structural units. In particular, R may be a saturated aliphatic organic moiety.

Particularly suitable hydroxyl-functionalized (meth)acrylates include hydroxyalkyl (meth)acrylates such as hydroxyethyl (meth)acrylate and hydroxypropyl (meth)acrylate and alkoxylated derivatives thereof wherein the hydroxyalkyl (meth)acrylate has been reacted with an alkylene oxide such as ethylene oxide and/or propylene oxide. Also suitable for use are polyalkylene glycol mono(meth)acrylates such as polyethylene glycol mono(meth)acrylates and polypropylene glycol mono(meth)acrylates. The length of the side chain in the polymer resulting from the incorporation of haloalkyl/haloalkenyl ether (meth)acrylate may be controlled and varied as may be desired to impart certain characteristics to the polymer by changing the length of the —R— group in the hydroxyl-functionalized (meth)acrylate used to prepare the haloalkyl/haloalkenyl ether (meth)acrylate. For example, if an alkoxylated hydroxyalkyl(meth) acrylate is employed, the degree of alkoxylation (the number of moles of alkylene oxide reacted per mole of hydroxyl functionality) may be varied from 1 (for a relatively short side chain) to 10 or higher (for a relatively long side chain).

Following reaction with a halogenated olefin, an active hydrogen of the hydroxyl-functionalized (meth)acrylate, polyol (e.g., diol) or partially masked polyol (e.g., diol) is replaced by a haloalkyl or haloalkenyl group (e.g., —CF=CH$_2$, —CF$_2$CFHCF$_3$, —CF$_2$CFClH, CF$_2$CClH$_2$, —CF$_2$CF$_2$H, —CH=CHCF$_3$ or —C(CF$_3$)=CH$_2$).

Without wishing to be bound by theory, it is believed that the above-described reaction proceeds by addition of a hydroxyl group of the hydroxyl-functionalized (meth)acrylate, polyol (e.g., diol) or partially masked polyol (e.g., diol) across the double bond of the halogenated olefin. Such reaction forms a halogenated alkyl group (i.e., the halogenated olefin is converted to a halogenated alkyl group which is present within the product formed), which may undergo an elimination (of HX, for example, where X is halogen) under certain conditions to yield haloalkenyl. Typically, the oxygen atom of the hydroxyl group becomes preferably bonded to the more "halogen heavy" carbon atom of the carbons involved in the carbon-carbon double bond of the halogenated olefin (i.e., the carbon having the greatest number of halogen atoms bonded to it or, if neither carbon has any halogen atoms bonded to it, the carbon having a haloalkyl substituent bonded to it containing the greatest number of halogen atoms). In certain cases, mixtures of different products are obtained, wherein the oxygen atom of the reacted hydroxyl group becomes bonded to each of the carbon atoms involved in the carbon-carbon double bond. As an alkenyl group may result from elimination of hydrohalide from the haloalkyl group under highly basic conditions, yields of product containing the haloalkyl group desired in the haloalkyl ether (meth)acrylate monomers used in certain embodiments of the present invention may be improved through the use of reaction conditions that are only mildly basic. If the production of a haloalkenyl ether (meth)acrylate is desired, then more basic reaction conditions may be employed.

In Method B, wherein a diol is employed as one of the reactants, it may be preferred to add the halogenated olefin incrementally to the polyol (e.g. diol) while reacting the two reactants so as to favor the production of the desired product (having one hydroxyl group that has reacted with the halogenated olefin to form a haloalkyl/haloalkenyl ether group and a hydroxyl group that remains unreacted so that it may then be converted to a (meth)acrylate functional group).

In Methods A and C, approximately stoichiometric amounts of the hydroxyl-functionalized (meth)acrylate (or partially masked polyol) and the halogenated olefin preferably are employed.

For instance, the active hydrogen-containing organic compound and the halogenated olefin may be reacted in a stoichiometric ratio of (moles active hydrogen-containing organic compound)/x:moles halogenated olefin, wherein x=number of active hydrogens per molecule of the active hydrogen-containing organic compound, of from about 1:8 to about 8:1, about 1:7 to about 7:1, about 1:6 to about 6:1, about 1:5 to about 5:1, about 1:4 to about 4:1, about 1:3 to about 3:1, about 1:2 to about 2:1, or about 1:1.5 to about 1.5:1, or about 1:1.1 to about 1.1:1.

In Method B, which utilizes a polyol (e.g., diol) as a reactant, it may be desirable to employ a stoichiometric excess of the polyol (e.g., diol) relative to the halogenated olefin so as to favor the production of a product in which a single hydroxyl group has been converted to a haloalkyl/haloalkenyl ether group over a product where all the hydroxyl groups have reacted with halogenated olefin. In such cases, the polyol and the halogenated olefin may be reacted in a stoichiometric ratio of (moles polyol):moles halogenated olefin of from about 1.5:1 to about 10:1 or about 2:1 to about 5:1. To the extent a mixture of product and unreacted polyol is produced, the mixture may be subjected to fractionation such that the unreacted polyol is separated and recycled for further reaction with halogenated olefin.

Optional Co-Monomers

Although in certain embodiments of the invention, a haloalkyl/haloalkenyl ether (meth)acrylate in accordance with the above description is homopolymerized or two or more haloalkyl/haloalkenyl ether (meth)acrylates are copolymerized to form a polymer, in other embodiments one or more such haloalkyl/haloalkenyl (meth)acrylates are copolymerized with one or more reactants (sometimes referred to herein as "co-monomers", although such reactants may be monomeric and/or oligomeric in structure) which are not haloalkyl/haloalkenyl ether (meth)acrylates as defined herein. Such reactants may generally contain one or more sites of ethylenic unsaturation capable of being co-polymerized with the carbon-carbon double bond(s) present in the haloalkyl/haloalkenyl (meth)acrylate(s), in particular sites of ethylenic unsaturation which are supplied by a (meth) acrylate functional group in the co-reactant. However, other types of ethylenically unsaturated co-monomers such as olefins, vinyl ethers, vinyl aromatic monomers and vinyl esters may also be employed.

Thus, in one embodiment of the invention, at least one haloalkyl/haloalkenyl ether (meth)acrylate is copolymerized with at least one (meth)acrylate-functionalized compound which is not a haloalkyl/haloalkenyl ether (meth)acrylate as defined herein. The resulting copolymer may be described as a polymer containing repeating units in its backbone or main chain derived from such monomers, wherein polymerization has taken place by reaction of the carbon-carbon double bonds of the (meth)acrylate groups. A (meth)acrylate-functionalized compound may be described as an organic compound bearing one or more (meth)acrylate functional groups per molecule. (Meth)acrylate-functionalized compounds suitable for use in the present invention may be generally described as ethylenically unsaturated compounds containing at least one carbon-carbon double bond alpha to an ester group (a compound containing at least one $\alpha,\beta$-unsaturated ester moiety), in particular a carbon-carbon double bond capable of participating in a free radical reaction or anionic reaction, in particular a reaction initiated by ultraviolet radiation or electron beam radiation. Such reactions may result in a polymerization or curing whereby the haloalkyl/haloalkenyl ether (meth)acrylate and (meth)acrylate-functionalized compound become part of a polymerized matrix or polymeric chain. In various embodiments of the invention, the (meth)acrylate-functionalized compound may contain one, two, three, four, five or more (meth)acrylate functional groups per molecule. Combinations of multiple (meth)acrylate-functionalized compounds containing different numbers of (meth)acrylate groups may be used, together with one or more haloalkyl/haloalkenyl ether (meth)acrylates, to prepare polymers in accordance with the present invention.

Curable compositions useful in preparing polymers in accordance with the present invention thus may contain one or more (meth)acrylate functional compounds, in addition to one or more haloalkyl/haloalkenyl ether (meth)acrylates, which are capable of undergoing free radical and/or anionic polymerization (curing) initiated by exposure to ultraviolet or electron beam radiation. Such (meth)acrylate-functionalized compounds may be oligomers or monomers or a combination of oligomer(s) and monomer(s).

Any of the following types of (meth)acrylate-functionalized compounds may, for example, be employed in curable compositions used to prepare polymers in accordance with the present invention, in combination with one or more haloalkyl/haloalkenyl ether (meth)acrylates as co-monomers: monomers such as (meth)acrylate esters of aliphatic mono-alcohols, (meth)acrylate esters of alkoxylated aliphatic mono-alcohols, (meth)acrylate esters of aliphatic polyols, (meth)acrylate esters of alkoxylated aliphatic polyols, (meth)acrylate esters of aromatic ring-containing alcohols, and (meth)acrylate esters of alkoxylated aromatic ring-containing alcohols; and oligomers such as epoxy (meth)acrylates, polyether (meth)acrylates, urethane (meth) acrylates, polyester (meth)acrylates (including amine- and sulfide-modified derivatives thereof); and combinations thereof.

Suitable (meth)acrylate-functionalized oligomers include, for example, polyester (meth)acrylates, epoxy (meth)acrylates, polyether (meth)acrylates, urethane (meth)acrylates (sometimes also referred to as polyurethane (meth)acrylates or urethane (meth)acrylate oligomers) and combinations thereof, as well as amine-modified and sulfide-modified variations thereof.

Exemplary polyester (meth)acrylates include the reaction products of acrylic or methacrylic acid or mixtures thereof with hydroxyl group-terminated polyester polyols. The reaction process may be conducted such that a significant concentration of residual hydroxyl groups remain in the polyester (meth)acrylate or may be conducted such that all or essentially all of the hydroxyl groups of the polyester polyol have been (meth)acrylated. The polyester polyols can be made by polycondensation reactions of polyhydroxyl functional components (in particular, diols) and polycarboxylic acid functional compounds (in particular, dicarboxylic acids and anhydrides). To prepare the polyester (meth) acrylates, the hydroxyl groups of the polyester polyols are then partially or fully esterified by reacting with (meth) acrylic acid, (meth)acryloyl chloride, (meth)acrylic anhydride or the like. Polyester (meth)acrylates may also be synthesized by reacting a hydroxyl-containing (meth)acrylate such as a hydroxyalkyl (meth)acrylate (e.g., hydroxyethyl acrylate) with a polycarboxylic acid. The polyhydroxyl functional and polycarboxylic acid functional components can each have linear, branched, cycloaliphatic or aromatic structures and can be used individually or as mixtures.

Examples of suitable epoxy (meth)acrylates include the reaction products of acrylic or methacrylic acid or mixtures thereof with glycidyl ethers or esters.

Exemplary polyether (meth)acrylate oligomers include, but are not limited to, the condensation reaction products of acrylic or methacrylic acid or mixtures thereof with polyetherols which are polyether polyols. Suitable polyetherols can be linear or branched substances containing ether bonds and terminal hydroxyl groups. Polyetherols can be prepared by ring opening polymerization of epoxides and other oxygen-containing heterocyclic compounds (e.g., ethylene oxide, 1,2-propylene oxide, butene oxide, tetrahydrofuran and combinations thereof) with a starter molecule. Suitable starter molecules include water, hydroxyl functional materials, polyester polyols and amines. Polyetherols may also be obtained by the condensation of diols such as glycols.

Urethane (meth)acrylates (sometimes also referred to as "polyurethane (meth)acrylates") capable of being used in the curable compositions and polymers of the present invention include urethanes based on aliphatic and/or aromatic polyester polyols, polyether polyols and polycarbonate polyols and aliphatic and/or aromatic polyester diisocyanates and polyether diisocyanates capped with (meth)acrylate end-groups.

In various embodiments, the urethane (meth)acrylates may be prepared by reacting aliphatic and/or aromatic polyisocyanates (e.g., diisocyanates, triisocyanates) with OH group terminated polyester polyols (including aromatic, aliphatic and mixed aliphatic/aromatic polyester polyols), polyether polyols, polycarbonate polyols, polycaprolactone polyols, polydimethysiloxane polyols, or polybutadiene polyols, or combinations thereof to form isocyanate-functionalized oligomers which are then reacted with hydroxyl-functionalized (meth)acrylates such as hydroxyethyl (meth) acrylate or hydroxypropyl (meth)acrylate to provide terminal (meth)acrylate groups. For example, the urethane (meth)acrylates may contain two, three, four or more (meth) acrylate functional groups per molecule. Other orders of addition may also be practiced to prepare the polyurethane (meth)acrylate, as is known in the art. For example, the hydroxyl-functionalized (meth)acrylate may be first reacted with a polyisocyanate to obtain an isocyanate-functionalized (meth)acrylate, which may then be reacted with an OH group terminated polyester polyol, polyether polyol, polycarbonate polyol, polycaprolactone polyol, polydimethysiloxane polyol, polybutadiene polyol, or a combination thereof. In yet another embodiment, a polyisocyanate may be first reacted with a polyol, including any of the aforementioned types of polyols, to obtain an isocyanate-functionalized polyol, which is thereafter reacted with a hydroxyl-functionalized (meth)acrylate to yield a polyurethane (meth)acrylate. Alternatively, all the components may be combined and reacted at the same time.

Any of the above-mentioned types of oligomers may be modified with amines or sulfides (e.g., thiols), following procedures known in the art. Such amine- and sulfide-modified oligomers may be prepared, for example, by reacting a relatively small portion (e.g., 2-15%) of the (meth) acrylate functional groups present in the base oligomer with an amine (e.g., a secondary amine) or a sulfide (e.g., a thiol), wherein the modifying compound adds to the carbon-carbon double bond of the (meth)acrylate in a Michael addition reaction.

Illustrative examples of suitable monomeric (meth)acrylate-functionalized compounds include (meth)acrylated mono- and polyols (polyalcohols) and (meth)acrylated alkoxylated mono-alcohols and polyols. The mono-alcohols and polyols may be aliphatic (including one or more cycloaliphatic rings) or may contain one or more aromatic rings (as in the case of phenol or bisphenol A). "Alkoxylated" means that the base mono-alcohol or polyol has been reacted with one or more epoxides such as ethylene oxide and/or propylene oxide so as to introduce one or more ether moieties (e.g., —$CH_2CH_2$—O—) onto one or more hydroxyl groups of the mono-alcohol or polyol, prior to esterification to introduce one or more (meth)acrylate functional groups. For example, the amount of epoxide reacted with the mono-alcohol or polyol may be from about 1 to about 30 moles of epoxide per mole of mono-alcohol or polyol. Examples of suitable mono-alcohols include, but are not limited to, straight chain, branched and cyclic C1-C54 mono-alcohols (which may be primary, secondary or tertiary alcohols). For instance, the mono-alcohol may be a C1-C7 aliphatic mono-alcohol. In another embodiment, the mono-alcohol may be a C8-C24 aliphatic mono-alcohol (e.g., lauryl alcohol, stearyl alcohol). Examples of suitable polyols include organic compounds containing two, three, four or more hydroxyl groups per molecule such as glycols (diols), e.g., ethylene glycol, 1,2- or 1,3-propylene glycol, or 1,2-, 1,3- or 1,4-butylene glycol, neopentyl glycol, trimethylolpropane, triethylolpropane, pentaerythritol, glycerol and the like.

Representative, but not limiting, examples of suitable monomeric (meth)acrylate-functionalized compounds include: 1,3-butylene glycol di(meth)acrylate, 1,4-butanediol di(meth)acrylate, 1,6-hexanediol di(meth)acrylate, longer chain aliphatic di(meth)acrylates (such as those generally corresponding to the formula $H_2C=CRC(=O)$—O—$(CH_2)_m$—O—C($=O$)CR'$=CH_2$, wherein R and R' are independently H or methyl and m is an integer of 8 to 24), alkoxylated (e.g., ethoxylated, propoxylated) hexanediol di(meth)acrylates, alkoxylated (e.g., ethoxylated, propoxylated) neopentyl glycol di(meth)acrylates, dodecyl di(meth) acrylates, cyclohexane dimethanol di(meth)acrylates, diethylene glycol di(meth)acrylates, dipropylene glycol di(meth) acrylates, alkoxylated (e.g., ethoxylated, propoxylated) bisphenol A di(meth)acrylates, ethylene glycol di(meth) acrylates, neopentyl glycol di(meth)acrylates, tricyclodecane dimethanol diacrylates, triethylene glycol di(meth)acrylates, tetraethylene glycol di(meth)acrylates, tripropylene glycol di(meth)acrylates, ditrimethylolpropane tetra(meth)acrylates, dipentaerythritol penta(meth)acrylates, alkoxylated (e.g., ethoxylated, propoxylated) pentaerythritol tetra(meth)acrylate, dipentaerythritol penta(meth)acrylates, pentaerythritol tetra(meth)acrylate, alkoxylated (e.g., ethoxylated, propoxylated) trimethylolpropane tri(meth) acrylates, alkoxylated (e.g., ethoxylated, propoxylated) glyceryl tri(meth)acrylates, trimethylolpropane tri(meth) acrylates, pentaerythritol tri(meth)acrylates, tris (2-hydroxy ethyl) isocyanurate tri(meth)acrylates, 2(2-ethoxyethoxy) ethyl (meth)acrylates, 2-phenoxyethyl (meth)acrylates, 3,3,5-trimethylcyclohexyl (meth)acrylates, alkoxylated lauryl (meth)acrylates, alkoxylated phenol (meth)acrylates, alkoxylated tetrahydrofurfuryl (meth)acrylates, caprolactone (meth)acrylates, cyclic trimethylolpropane formal (meth)acrylates, sdicyclopentadienyl (meth)acrylates, diethylene glycol methyl ether (meth)acrylates, alkoxylated (e.g., ethoxylated, propoxylated) nonyl phenol (meth)acrylates, isobornyl (meth)acrylates, isodecyl (meth)acrylates, isooctyl (meth)acrylates, lauryl (meth)acrylates, methoxy polyethylene glycol (meth)acrylates, octyldecyl (meth)acrylates (also known as stearyl (meth)acrylates), tetrahydrofurfuryl (meth) acrylates, tridecyl (meth)acrylates, triethylene glycol ethyl ether (meth)acrylates, t-butyl cyclohexyl (meth)acrylates, dicyclopentadiene di(meth)acrylates, phenoxyethanol (meth)acrylates, octyl (meth)acrylates, decyl (meth)acrylates, dodecyl (meth)acrylates, tetradecyl (meth)acrylates, cetyl (meth)acrylates, hexadecyl (meth)acrylates, behenyl (meth)acrylates, diethylene glycol ethyl ether (meth)acrylates, diethylene glycol butyl ether (meth)acrylates, triethylene glycol methyl ether (meth)acrylates, dodecanediol di (meth)acrylates, dipentaerythritol penta/hexa(meth)acrylates, pentaerythritol tetra(meth)acrylates, alkoxylated (e.g., ethoxylated, propoxylated) pentaerythritol tetra(meth)acrylates, di-trimethylolpropane tetra(meth)acrylates, alkoxylated (e.g., ethoxylated, propoxylated) glyceryl tri(meth) acrylates, and tris (2-hydroxy ethyl) isocyanurate tri(meth) acrylates, and combinations thereof.

The relative proportions of haloalkyl/haloalkenyl ether (meth)acrylate(s) and (meth)acrylate-functionalized compound(s) utilized in the curable compositions and polymers derived therefrom may be varied as may be appropriate depending upon the particular components selected and the properties of the curable composition and the cured composition (polymer) obtained therefrom which are desired. For example, in various embodiments of the invention, the weight amount in total of haloalkyl/haloalkenyl ether (meth) acrylate (which may be a single haloalkyl/haloalkenyl ether (meth)acrylate or a combination of two or more different haloalkyl/haloalkenyl ether (meth)acrylates) may be from 0.03 to 99% by weight or from 0.03 to 10% by weight or from 10 to 20% by weight or from 20 to 30% by weight or from 30 to 40% by weight or from 40 to 50% by weight or from 50 to 60% by weight or from 60 to 70% by weight or from 70 to 80% by weight or from 80 to 90% by weight or from 90 to 99% by weight and the weight amount in total of (meth)acrylate-functionalized compound (which may be a single (meth)acrylate-functionalized compound or a combination of two or more different (meth)acrylate-functionalized compounds) may correspondingly be from 1 to 99% by weight or from 10 to 90% by weight, based on the combined total weight of haloalkyl/haloalkenyl ether (meth)acrylate and (meth)acrylate-functionalized compound.

Halogenated (meth)acrylates other than haloalkyl/haloalkenyl ether (meth)acrylates are also suitable for use as co-monomers in preparing the polymers of the present invention. As used herein, the term halogenated (meth)acrylate refers to an organic compound comprising an acrylate (—O—C(=O)CH=CH$_2$) or methacrylate (—O—C(=O)C(CH$_3$)=CH$_2$) functional group and at least one halogen atom (F, Cl, Br, I). In one embodiment, the halogenated (meth)acrylate comprises a single (meth)acrylate functional group. The halogenated (meth)acrylate may comprise two, three, four, five or more halogen atoms, which may be the same as or different from each other. In certain embodiments, the only halogen present in the halogenated (meth)acrylate is fluorine. In other embodiments, the halogenated (meth)acrylate is perhalogenated (e.g., perfluorinated) such that every carbon atom other than the carbon atoms present in the (meth)acrylate functional group is substituted by halogen (e.g., fluorine) only, with no hydrogen being substituted on such carbon atom(s). The halogenated (meth)acrylate may correspond to the general structure R$^1$—O—C(=O)CR=CH$_2$, wherein R is hydrogen or methyl and R$^1$ is an organic moiety comprising one or more halogen substituents, such as a halogenated alkyl group, a halogenated cycloalkyl group, a halogenated aryl group, or a halogenated aralkyl group. Such organic moieties may comprise one or more substituents other than halogen substituents, including for example alkoxy, cyano, nitro or carboxylate substituents. R$^1$ may be perhalogenated, in particular perfluorinated.

Suitable fluorine-containing acrylate and methacrylate co-monomers include, for example, 2-fluoroethyl acrylate and 2-fluoroethyl methacrylate; 1,1,1,3,3,3-hexafluoro-isopropyl acrylate and 1,1,1,3,3,3-hexafluoro-iso-propyl methacrylate; 1,1-dihydroperfluoroalkyl acrylates and methacrylates of the general structure, CF$_3$(CF$_2$)$_n$CH$_2$OC(=O)C(R)=CH$_2$, in which R is hydrogen or methyl and n is typically 0 to 12, such as, 2,2,2-trifluoroethyl acrylate and 2,2,2-trifluoroethyl methacrylate, 2,2,3,3,3-pentafluoropropyl acrylate and 2,2,3,3,3-pentafluoropropyl methacrylate, 1H,1H-heptafluorobutyl acrylate and 1H,1H-heptafluorobutyl methacrylate, 1H,1H-perfluoropentyl acrylate and 1H,1,H-perfluoropentyl methacrylate, 1H, 1H-perfluorohexyl acrylate and 1H,1,H-perfluorohexyl methacrylate, 1H, 1H-perfluorooctyl acrylate and 1H,1,H-perfluorooctyl methacrylate, 1H, 1H-perfluorodecyl acrylate and 1H,1,H-perfluorodecyl methacrylate, 1H, 1H-perfluorododecyl acrylate and 1H,1,H-perfluorododecyl methacrylate; 1,1,2,2-tetrahydroperfluoroalkyl acrylates and methacrylates of the general structure CF$_3$(CF$_2$)$_n$(CH$_2$)$_2$OCOC(R)=CH$_2$, in which R is hydrogen or methyl and n' is typically 0 to 11, such as 3,3,4,4,4-pentafluorobutyl acrylate and 3,3,4,4,4-pentafluorbutyl methacrylate, 1H,1H,2H,2H-perfluorohexyl acrylate, 1H,1H,2H,2H-perfluorohexyl methacrylate, 1H,1H,2H,2H-perfluorooctyl acrylate, 1H,1H,2H,2H-perfluorooctyl methacrylate, 1H,1H,2H,2H-perfluorodecyl acrylate and 1H,1H, 2H,2H-perfluorodecyl methacrylate, and 1H,1H,2H,2H-perfluorododecyl acrylate and 1H,1H,2H,2H-perfluorododecyl methacrylate; 1,1,Ω-trihydroperfluoroalkyl acrylates and methacrylates of the general structure CHF$_2$(CF$_2$)$_n$(CH$_2$)$_2$OCOC(R)=CH$_2$. in which in which R is hydrogen or methyl and n" is typically 0 to 12, such as 2,2,3,3-tetrafluoropropyl acrylate and 2,2,3,3-tetrafluoropropyl methacrylate, 1H,1H,5H-perfluoropentyl acrylate and 1H,1H,5H-perfluoropentyl methacrylate, 1H,1H,7H-perfluoroheptyl acrylate and 1H,1H,7H-perfluoroheptyl methacrylate, 1H,1H,9H-perfluorononly acrylate and 1H,1H,9H-perfluorononyl methacrylate, 1H,1H,11H-perfluoroundecyl acrylate and 1H,1H,11H-perfluoroundecyl methacrylate; 2,2,3,4,4,4-hexafluorobutyl acrylate and 2,2,3,4,4,4-hexafluorobutyl methacrylate, perfluorocyclohexyl methyl acrylate and perfluorocyclohexyl methyl methacrylate, 3-(trifluoromethyl) benzyl acrylate and 3-(trifluoromethyl) benzyl methacrylate, pentafluorophenyl acrylate and pentafluorophenyl methacrylate; pentafluorobenzyl acrylate and pentafluorobenzyl methacrylate; pentafluorobenzyl acrylate and pentafluorobenzyl methacrylate; and mixtures thereof.

In certain embodiments, the polymer does not contain any monomer other than haloalkyl/haloalkenyl ether (meth)acrylate (i.e., the haloalkyl/haloalkenyl ether (meth)acrylate or mixture of haloalkyl/haloalkenyl ether (meth)acrylates constitutes 100% by weight of the polymer). In other embodiments, however, the polymer comprises up to 99.7%, up to 99%, up to 97%, up to 95%, up to 90%, up to 80%, up to 70%, up to 60%, up to 50%, up to 40%, up to 30%, up to 20%, up to 10%, up to 5% or up to 1% by weight of one or more co-monomers other than haloalkyl/haloalkenyl ether (meth)acrylate. For example, the polymer may be comprised of from 0.1 to 99% by weight of one or more monomer(s) other than haloalkyl/haloalkenyl ether (meth)acrylate.

Where the polymer of the present invention is a copolymer, the arrangement of the polymerized co-monomers along the polymer backbone, in the copolymer of the present invention, depends on the kinetics of the polymerization and may take several forms. One preferred arrangement is that of an alternating copolymer, with a regular alternation of the different co-monomers. Alternating copolymers of fluoroalkyl/fluoroalkenyl ether (meth)acrylates and fluorinated (meth)acrylate co-monomers are especially preferred as these would be expected to have superior resistance to free radical, oxidative, or photooxidative attack, such as might be desirable for materials used in exterior coatings, battery component, photovoltaic devices, energy storage devices, membranes, and filtration devices.

Another preferred arrangement of comonomers along the copolymer backbone is that of a random copolymer (which may also be referred to as a statistical copolymer). The structures of random copolymers are typically determined by the reaction kinetics of the different monomers being reacted during the copolymerization. The random copolymer may, in one embodiment of the invention, have a linear structure, but in other embodiments may have a branched or even crosslinked structure.

Still another preferred arrangement of comonomers along the copolymer backbone is that of a block copolymer. Such block copolymers may, for example, be comprised of at least one block of a first haloalkyl/haloalkenyl ether (meth)acrylate and at least one block of a second haloalkyl/haloalkenyl ether (meth)acrylate or a co-monomer other than a haloalkyl/haloalkenyl ether (meth)acrylate and may be either linear or branched (radial) in structure. In various embodiments, the block copolymer may, for example, have any of the following structures: A-B; A-B-A; B-A-B; A-B-A-B; or A-B-A-B-A, wherein A is a block of haloalkyl/haloalkenyl ether (meth)acrylate in polymerized form (i.e., a poly(haloalkyl/haloalkenyl ether (meth)acrylate) block) and B is a block of (meth)acrylate-functionalized co-monomer other than a haloalkyl/haloalkenyl ether (meth)acrylate (e.g., a block of non-halogenated (meth)acrylate (i.e., a poly(non-halogenated (meth)acrylate) or a block of halogenated (meth)acrylate (i.e., a poly(halogenated (meth)acrylate)).

Gradient copolymers are also considered to be within the scope of the present invention, as are crosslinked copolymers (particularly where a haloalkyl/haloalkenyl ether (meth)acrylate has been reacted with a (meth)acrylate-functionalized compound containing two or more (meth)acrylate functional groups per molecule or a mixture of (meth)acrylate-functionalized compounds containing at least some amount of (meth)acrylate-functionalized compound(s) containing two or more (meth)acrylate functional groups per molecule.

In certain embodiments of the invention, the polymer (including any copolymer described herein) has a number average molecular weight of 5000 to 2,000,000 (e.g., 5000 to 1,500,000, or 5000 to 800,000, or 5,000 to 300,000) daltons or even higher, as measured by gel permeation chromatography using polystyrene standards. The polymer or copolymer may be thermoplastic, thermoset or elastomeric, depending upon the constituents and polymerization (curing) methods used to prepare it.

In other embodiments of the invention, the polymer (including any copolymer described herein) has a number average molecular weight of 5000 to 2,000,000 (e.g., 5000 to 1,500,000, or 5000 to 800,000, or 5,000 to 300,000) daltons or even higher, as measured by gel permeation chromatography using polystyrene standards. For example poly (1,1,2-trifluoro-2-chloroethoxyethylmethacrylate) that is from monomer, 1,1,2-trifluoro-2-chloroethoxyethylmethacrylate, which is the product of 1,1,2-trifluoro-2-chloroethylene (CTFE) and hydroxyethyl methacrylate or 2-hydroxyethyl methacrylate (HEMA) prepared according to Method A, can be dissolved in a solvent such as tetrahydrofuran (THF), and the concentration of polymer can be as high as 40 wt % based on the total weigh of the polymer and solvent. It is desirable to make a film using a polymer containing solution on glass, metal, plastic etc. Other solvents can be chosen from for example toluene, acetone butanone (also known as methyl ethyl ketone or 'MEK'), cyclohexanone, nitroethane, chloroform, dichloromethane (or methylene chloride), benzene, chlorobenzene, xylene, methoxybenzene (also named anisole or phenyl methyl ether), diethyl phthalate, methoxypropyl acetate, ethyl acetate, ethyl lactate, methyl acetate, methyl formate, trans-1,2-dichloroethylene, trans-1-chloro-3,3,3-fluoropropene, cis-1-chloro-3,3,3-fluoropropene, 2-chloro-3,3,3-fluoropropene, cis-1,1,1,4,4,4-hexafluorobutene, 1,1,1,3,3-tetrafluorobutane, formic acid, and mixture thereof.

In certain embodiments of the invention, the polymer (including any copolymer described herein) has refractive index of from about 1.339 to about 1.700, measured by technology known to those skilled in the art, preferably 1.400 to 1.600. For example poly (1,1,2-trifluoro-2-chloroethoxyethylmethacrylate) that is from monomer, 1,1,2-trifluoro-2-chloroethoxyethylmethacrylate, which is the product of 1,1,2-trifluoro-2-chloroethylene (CTFE) and hydroxyethyl methacrylate or 2-hydroxyethyl methacrylate (HEMA) prepared according to Method A, has refractive index of about 1.453. Polymethylmethacrylate (PMMA) has refractive index of 1.491, copolymer of 1,1,2-Trifluoro-2-chloroethoxyethylmethacrylate and methylmethacrylate can have refractive index of between 1.453 and 1.491 depending on the ratio of 1,1,2-Trifluoro-2-chloroethoxyethylmethacrylate to methylmethacrylate, for example 99:1 to 89:11 or 89:11 to 79:21 or 79:21 to 69:31 or 69:30 to 59:41 or 59:41 to 49:51 or 49:51 to 39:61 or 39:61 to 29:71 or 29:71 to 19:81 or 19:811 to 9:91 or 9:91 to 1:99. A low refractive index is necessary for optical film applications, adhesives for optical elements such as films for displays like LED, LCD, and etc. Particularly, the refractive index gradient between homopolymers and copolymers of the present invention make the polymers suitable for optical fiber material components such as core or cladding or packaging.

Poly (1,1,2-trifluoro-2-chloroethoxyethylmethacrylate) that is from monomer, 1,1,2-trifluoro-2-chloroethoxyethylmethacrylate, which is the product of 1,1,2-trifluoro-2-chloroethylene (CTFE) and hydroxyethyl methacrylate or 2-hydroxyethyl methacrylate (HEMA) prepared according to Method A, has a number average molecular weight of 5000 to 2,000,000 (e.g., 5000 to 1,500,000, or 5000 to 800,000, or 5,000 to 300,000) daltons or even higher, as measured by gel permeation chromatography using polystyrene standards. The polymer has a glass transition temperature ($T_g$) of about 16 to 19° C. as measured by DSC known by those skilled in the art. Glass transition temperature of a copolymer of 1,1,2-trifluoro-2-chloroethoxyethylmethacrylate and methyl methacrylate (MMA) is typically lower than poly methyl methacrylate, for example, the glass transition temperature of polymer of 80 wt % MMA and 20 wt % 1,1,2-trifluoro-2-chloroethoxyethylmethacrylate is about 15° C. lower that PMMA of similar molecular weight.

Curing Agents

The curable compositions of the present invention may optionally comprise one or more curing agents, which may be any of the substances known in the art to be capable of initiating polymerization (curing) of ethylenically unsaturated compounds or accelerating the rate at which such polymerization takes place. Such substances may variously be referred to as curing agents, curatives, initiators, promoters or accelerators.

If the curable composition is to be cured using light, such as ultraviolet light, it will generally be desirable to formulate the composition to include one or more photoinitiators. However, if electron beam or chemical curing is employed, then the curable composition need not contain any photoinitiator.

A photoinitiator is a compound that undergoes a photoreaction on absorption of light, producing reactive species. The reactive species which are generated then initiate polymerization of the reactive components of the curable composition, e.g., the (meth)acrylate-functionalized compound(s). Generally speaking, such polymerization (curing) involves reaction of the carbon-carbon double bonds present in such components. The reactive species may be, for example, a free radical species or an anionic species, in various embodiments of the invention. The photoinitiator may be a photobase generator such as an α-aminoacetophenone, in one embodiment of the invention.

Suitable photoinitiators include, for example, alpha-hydroxy ketones, phenylglyoxylates, benzyldimethylketals, alpha-aminoketones, mono-acyl phosphines, bis-acyl phosphines, metallocenes, phosphine oxides, benzoin ethers and benzophenones and combinations thereof.

If photoinitiator is employed in the curable composition, it may generally be present in a total concentration of up to about 15% by weight based on the total weight of the curable composition (e.g., a concentration of from about 0.1 to about 5% by weight based on the total weight of the curable composition).

One or more peroxides may be present in the curable composition as curing agents. As used herein, the term "peroxide" includes both organic and inorganic substances containing peroxy (—O—O—) functionality such as, for example, hydrogen peroxide, percarbonates, peresters, percarboxylic acids, organic hydroperoxides, dialkyl peroxides and the like and combinations. Such peroxides may be used in combination with one or more accelerators, such as various transition metal compounds. A redox system comprising one or more peroxides may be employed in combination with the curable compositions of the present invention. Other chemical curing agents besides peroxides which are known in the art of polymerizing ethylenically unsaturated monomers, particularly (meth)acrylate-functionalized monomers may also or alternatively be present in the curable compositions of the present invention.

Curing of the composition may be achieved by a polymerization reaction involving the carbon-carbon double bonds of the (meth)acrylate functional groups of the haloalkyl/haloalkenyl ether (meth)acrylates. Where the composition includes a haloalkenyl ether (meth)acrylate, the alkenyl functional groups may also, at least under certain curing conditions and depending upon the reactivity of the alkenyl functional groups, participate in the polymerization reaction.

Other Components

The curable compositions of the present invention may optionally contain one or more additives instead of or in addition to the above-mentioned ingredients. Such additives include, but are not limited to, antioxidants, ultraviolet absorbers, photostabilizers, foam inhibitors, flow or leveling agents, colorants, pigments, dispersants (wetting agents), slip additives, fillers, thixotropic agents, matting agents, thermoplastics such as acrylic resins that do not contain any polymerizable functional groups, waxes or other various additives, including any of the additives conventionally utilized in the coating, sealant, adhesive, molding or ink arts.

Curing of and Uses for the Curable Compositions

The curable compositions of the present invention are useful in many different applications, such as inks (in graphic arts applications, including for food packaging), molding resins, 3D printing resins, coatings (e.g., fiber optic coatings), sealants and adhesives (e.g., UV-curable laminating adhesives, UV-curable hotmelt adhesives), and in composites, among other potential applications.

Cured compositions prepared from curable compositions as described herein may be used, for example, in three-dimensional articles (wherein the three-dimensional article may consist essentially of or consist of the cured composition), coated articles (wherein a substrate is coated with one or more layers of the cured composition), laminated or adhered articles (wherein a first component of the article is laminated or adhered to a second component by means of the cured composition), or printed articles (wherein graphics or the like are imprinted on a substrate, such as a paper, plastic or metal substrate, using the cured composition).

The curable compositions may be subjected to curing by means of free radical polymerization or other types of polymerization (e.g., anionic or cationic polymerization).

Curing of the curable compositions in accordance with the present invention may be carried out by any suitable method, such as free radical, cationic and/or anionic polymerization. One or more initiators, such as a free radical initiator (e.g., photoinitiator, peroxide initiator) may be present in the curable composition. Prior to curing, the curable composition may be applied to a substrate surface in any known conventional manner, for example, by spraying, knife coating, roller coating, casting, drum coating, dipping, and the like and combinations thereof. Indirect application using a transfer process may also be used. A substrate may be any commercially relevant substrate, such as a high surface energy substrate or a low surface energy substrate, such as a metal substrate or plastic substrate, respectively. The substrates may comprise metal, paper, cardboard, glass, thermoplastics such as polyolefins, polycarbonate, acrylonitrile butadiene styrene (ABS), and blends thereof, composites, wood, leather and combinations thereof. When used as an adhesive, the curable composition may be placed between two substrates and then cured, the cured composition thereby bonding the substrates together.

Curing may be accelerated or facilitated by supplying energy to the curable composition, such as by heating the curable composition and/or by exposing the composition to a radiation source, such as visible or UV light, infrared radiation, and/or electron beam radiation. Thus, the cured composition may be deemed the reaction product of the curable composition, formed by curing, and comprising a polymer in accordance with the present invention.

Polymers in accordance with the present invention can be used in a wide variety of applications. For example, the polymers can be utilized as compatibilizing agents, foaming agents, surfactants, or low surface energy additives (for anti-stain, anti-soil, or anti-stick applications, for wetting or coating applications, and anti-fouling applications), to improve or enhance solvent or chemical resistance (in coatings, films, fabricated parts, etc.), in the preparation of oil and water repellant surfaces (for substrates such as plastics, textiles, paper, wood, leather, and the like), as coatings for medical devices, as lubricants, as additives and bulk materials for electronic applications, as or in thermoplastic elastomers, as impact modifiers, as adhesives, for drug (or pharmaceutical) delivery, in cosmetic applications, and many others as will be evident to those skilled in the art.

Polymers (including copolymers) may be low surface energy polymers useful for modifying the surface energy of polymeric materials. These polymers can be used in additive amounts or used as bulk materials. Additive amounts may be included in a wide variety of bulk polymers to impart properties such as stain resistance that are not inherent in the bulk polymers. Potential applications include food uses, textiles, coatings (e.g., acrylic-based coatings), pharmaceuticals, paints (e.g., acrylic-based paints), and many other industries. Reduction of surface energy by the polymer of the present invention may be characterized by water contact angle, a technology known by those skilled in the art. It is desirable that the water contact angle increase is more than about 5 degree, more desirable more than about 8 degree, even more desirable more than about 15 degree. Contact angle increase is the difference between a polymer comprising haloalkyl/haloalkenyl ether (meth)acrylates and a polymer without haloalkyl/haloalkenyl group.

The polymers provided by the present invention (including low surface energy copolymers) may be used in combination with any of the thermoplastic and thermosetting resins conventionally used in coating compositions. Of course, the specific resin or resins employed should be chosen to be appropriate for the coating application involved and should be compatible with the other components of the coating composition. Examples of useful resins include latexes, acrylic resins, vinyl acrylic resins, vinyl acetate resins, alkyd resins, polyester resins, polyurethane resins, epoxy resins, vinyl resins, phenoxy resins and the like. In the event that the final coating resin is to be a thermoset coating, the resin component includes an effective amount of a crosslinking component, e.g., at least one crosslinking agent, such as the conventionally used melamine/formaldehyde resins, urea/formaldehyde resins and the like. One or more such crosslinking agents are employed in combination with one or more other resins, referred to as thermosetting resins, in an amount effective to form crosslinks in the thermosetting resin or resins, e.g., upon the application of heat, to form the final desired thermoset surface coating.

Additionally, there exists a significant opportunity to utilize polymers in accordance with the present invention as hydrophobic additives to provide repellency characteristics to coatings, fibers and films. A key aspect of such products is that they may be added during melt processing and thereby eliminate subsequent treatment steps. The most attractive applications for such hydrophobic additives are in textiles, coatings and films, and key product attributes in these applications are anti-stain, anti-smudge, and water repellent features. Polymers in accordance with the present invention are expected to effectively function in a variety of applications involving the modification of the surface chemistry of polymeric articles. Currently, some fluorinated materials are used for such applications, but such fluorinated materials are under significant regulatory pressure to be phased out.

Areas of particular interest include, but are but not limited to: 1) repellency applications in the textile, coating and paint application, wherein the polymers in accordance with the present invention may be used for the preparation of stain and moisture repellent fibers, films, sheets, coatings and paints and the like for residential and commercial uses; 2) self-adhesive applications including release liners in particular, wherein liners are coated for label stock and graphic arts markets, i.e., for calendered kraft papers and polyethylene-coated papers, and film liners; 3) mold release agents; 4) fluorochemical surfactants; 5) printable/paintable polyolefins; 6) protective window treatments; 7) antigraffiti coatings; 8) aircraft coatings; 9) anticondensate additives; 10) abrasion resistance additives; and encapsulation of circuit board to improve its moisture, dust, and corrosion resistance.

Illustrative Aspects of the Present Invention

Various exemplary aspects of the present invention may be summarized as follows:

Aspect 1: A polymer comprising, in polymerized form, at least one haloalkyl/haloalkenyl ether (meth)acrylate comprising a haloalkyl or haloalkenyl moiety bonded through an ether linkage and an organic spacer moiety to a (meth)acrylate functional group.

Aspect 2: The polymer of Aspect 1 comprising, in polymerized form, at least one haloalkyl ether (meth)acrylate corresponding to general structure (I):

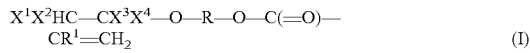

$$X^1X^2HC\text{—}CX^3X^4\text{—}O\text{—}R\text{—}O\text{—}C(=O)\text{—}CR^1=CH_2 \quad (I)$$

wherein R is an organic moiety, $X^1$, $X^2$, $X^3$ and $X^4$ are independently selected from hydrogen, halogen, alkyl or haloalkyl, subject to the proviso that at least one of $X^1$, $X^2$, $X^3$ or $X^4$ is halogen or a haloalkyl group, and $R^1$ is hydrogen or methyl.

Aspect 3: The polymer of Aspect 2, wherein the polymer comprises, in polymerized form, at least one haloalkyl ether (meth)acrylate corresponding to general structure (I) wherein at least two of $X^1$, $X^2$, $X^3$ or $X^4$ are selected from the group consisting of halogens and haloalkyl groups.

Aspect 4: The polymer of Aspect 2 or 3, wherein the polymer comprises, in polymerized form, at least one haloalkyl ether (meth)acrylate corresponding to general structure (I) wherein at least two of $X^1$, $X^2$, $X^3$ or $X^4$ are selected from the group consisting of fluorine and fluoroalkyl groups.

Aspect 5: The polymer of Aspect 2 or 3, wherein the polymer comprises, in polymerized form, at least one haloalkyl ether (meth)acrylate corresponding to general structure (I) wherein at least one of $X^1$, $X^2$, $X^3$ or $X^4$ is fluorine or a fluoroalkyl group.

Aspect 6: The polymer of any of Aspects 2 to 5, wherein the polymer comprises, in polymerized form, at least one haloalkyl ether (meth)acrylate corresponding to general structure (I) wherein each of $X^1$, $X^2$, $X^3$ and $X^4$ is halogen or a haloalkyl group.

Aspect 7: The polymer of any of Aspects 2 to 6, wherein the polymer comprises, in polymerized form, at least one haloalkyl ether (meth)acrylate corresponding to general structure (I) wherein one of $X^1$, $X^2$, $X^3$ or $X^4$ is a C1-C8 haloalkyl group.

Aspect 8: The polymer of any of Aspects 2 to 7, wherein the polymer comprises, in polymerized form, at least one haloalkyl ether (meth)acrylate corresponding to general structure (I) wherein one of $X^1$, $X^2$, $X^3$ or $X^4$ is a C1-C8 fluoroalkyl group.

Aspect 9: The polymer of Aspect 2, wherein the polymer comprises, in polymerized form, at least one haloalkyl ether (meth)acrylate corresponding to general structure (I) wherein a) $X^1$ is chlorine and $X^2$, $X^3$ and $X^4$ are fluorine or b) $X^3$ is chlorine and $X^1$, $X^2$ and $X^4$ are fluorine.

Aspect 10: The polymer of any of Aspects 2 to 9, wherein the polymer comprises, in polymerized form, at least one haloalkyl ether (meth)acrylate corresponding to general structure (I) wherein R is an alkylene segment or a poly(oxyalkylene) segment.

Aspect 11: The polymer of any of Aspects 2 to 10, wherein the polymer comprises, in polymerized form, at least one haloalkyl ether (meth)acrylate corresponding to general structure (I) wherein R is an ethylene segment or a poly(oxyethylene) segment.

Aspect 12: The polymer of any of Aspects 2 to 11, wherein the polymer comprises, in polymerized form, at least one haloalkyl ether (meth)acrylate corresponding to general structure (I) wherein R is —[CH$_2$CH$_2$O]$_n$—CH$_2$CH$_2$— and n is 0 or an integer of from 1 to 10.

Aspect 13: The polymer of any of Aspects 2 to 12, wherein the moiety $X^1X^2HC$—$CX^3X^4$—O—R—O— has a molecular weight not greater than 900 daltons.

Aspect 14: The polymer of any of Aspects 2 to 13, wherein R is a non-halogenated organic moiety.

Aspect 15: The polymer of any of Aspects 2 to 14, wherein R is an aliphatic organic moiety, optionally containing one or more oxygen atoms.

Aspect 16: The polymer of any of Aspects 2 to 15, wherein R is a saturated aliphatic organic moiety, optionally containing one or more ether oxygen atoms.

Aspect 17: The polymer of any of Aspects 2 to 16, wherein the polymer is a copolymer of a) the at least one haloalkyl/haloalkenyl ether (meth)acrylate and b) at least one (meth)acrylate-functionalized compound other than a haloalkyl/alkenyl ether (meth)acrylate comprising a haloalkyl moiety bonded through an ether linkage and an organic spacer moiety to a (meth)acrylate functional group.

Aspect 18: A curable composition comprising a) at least one haloalkyl/haloalkenyl ether (meth)acrylate comprising a haloalkyl or haloalkenyl moiety bonded through an ether linkage and an organic spacer moiety to a (meth)acrylate functional group (such as, for example, a haloalkyl/haloalkenyl ether (meth)acrylate corresponding to general structure (I) as further specified in any of Aspects 2 to 16) and b) at least one of i) a (meth)acrylate-functionalized compound other than a haloalkyl/haloalkenyl ether (meth)acrylate comprising a haloalkyl or haloalkenyl moiety bonded through an ether linkage and an organic spacer moiety to a (meth) acrylate functional group or ii) a curing agent.

Aspect 19: The curable composition of Aspect 18, additionally comprising at least one co-monomer which is not a haloalkyl/haloalkenyl ether (meth)acrylate.

Aspect 20: A method of making a polymer, comprising polymerizing one or more monomers comprised of at least one haloalkyl/haloalkenyl ether (meth)acrylate which is comprised of a haloalkyl or haloalkenyl moiety bonded through an ether linkage (such as, for example, a haloalkyl/haloalkenyl ether (meth)acrylate corresponding to general structure (I) as further specified in any of Aspects 2 to 16) and an organic spacer moiety to a (meth)acrylate functional group.

Aspect 21: Use of a polymer in accordance with any of Aspects 1 to 17 in an application selected from the group consisting of adhesives, coatings, paints, sealants, fibers, textiles, molded articles, films, sheets, laminates, and composites.

Aspect 22: An article of manufacture comprising at least one polymer in accordance with any of Aspects 1 to 17.

Within this specification, embodiments have been described in a way which enables a clear and concise specification to be written, but it is intended and will be appreciated that embodiments may be variously combined or separated without departing from the invention. For example, it will be appreciated that all preferred features described herein are applicable to all aspects of the invention described herein.

In some embodiments, the invention herein can be construed as excluding any element or process step that does not materially affect the basic and novel characteristics of the polymer, curable composition or process for making or using the polymer or curable composition. Additionally, in some embodiments, the invention can be construed as excluding any element or process step not specified herein.

Although the invention is illustrated and described herein with reference to specific embodiments, the invention is not intended to be limited to the details shown. Rather, various modifications may be made in the details within the scope and range of equivalents of the claims and without departing from the invention.

Example: 1 Reaction of
1,1,2-Trifluoro-2-chloroethylene (CTFE) with
2-Hydroxyethylmethacrylate (HEMA) in 30%
Acetone and 70% DMSO Solvent A 1 L four-neck (14/20) flask with overhead stirring and equipped with a digital thermometer and a dry-ice condenser with outlet connected to a nitrogen source was used. A pre-punctured septum was placed on the remaining neck. The reaction flask was charged with 2-Hydroxyethylmethacrylate (80.22 g/0.6160 mol), DMSO (374.66 g/4.7953 mol), acetone (161.55 g/2.7774 moles), potassium carbonate (94.03 g/0.6803 mol) and benzoquinone (0.76/7.03×10$^{-3}$ mol). The reaction mixture was stirred while CTFE (78.92 g/0.6776 mol) was added subsurface in aliquots through a septum over two days with the temperature ranging from 16-21° C. An internal standard (α,α,α-trifluorotoluene) was added to the reaction mixture to follow the reaction by FNMR.

The reaction mixture was charged to a 5 L separatory funnel with 2 L of water and 1 L of dichloromethane and stirred for 10 minutes. The stirring was stopped and two immiscible layers formed after sitting for 15 minutes. The resulting layers were separated and the bottom organic layer was washed twice with 1 L of water. The organic layer was separated and the solvent stripped at reduced pressure to isolate the product. The amount of crude 2-Chloro-1,1,2-trifluoroethoxy methacrylate product isolated was 120.90 g. The product had a purity of 73 wt % and a yield of 58% by FNMR based on 2-Hydroxymethacrylate starting material.

The crude material was purified by column chromatography using a 2"×24" column packed with silica gel. The ratio of silica to crude material was 15:1. The product was eluted with 10% ethyl acetate/n-hexane. The crude material was purified in multiple batches. The combined purified product was 66.99 grams and was 97% pure by GC A %. The product was also confirm by GC/MS and LC/MS. The yield of purified product was 43% based on 2-Hydroxymethacrylate starting material.

$^{19}$F NMR (CDCl$_3$): δ −88.26 ppm (F$_A$), −88.74 ppm (F$_B$)*, (q of d of d, $^2J_{Fa\text{-}Fb}$=−141 Hz, $^3J_{Fa\text{-}H}$=3.5 Hz, $^3J_{Fb\text{-}H}$=4.7 Hz), δ −154.31 (Fe) (d of t, $^3J_{F\text{-}F}$=12 Hz, $^2J_{F\text{-}H}$=48

$^1$HNMR (CDCl$_3$): δ 1.95 ppm (d of d, 3H); δ 4.20 ppm (d of d of d, 2H); δ 4.40 (d of d of d, 2H); δ 5.60 (d of m 1H) δ 6.08 ppm (d of d of d, 1H, $^2J_{H\text{-}F}$=48, $^3J_{H\text{-}Fa}$=3.5 Hz, $^3J_{H\text{-}Fb}$=4.7 Hz); δ 6.10 ppm (d of m, 1H)

* The chemical shifts of F$_A$ and F$_B$ were calculated from the AB type quartet.

Example 2: Reaction of
1,1,2-Trifluoro-2-chloroethylene (CTFE) with
2-Hydroxyethylmethacrylate (HEMA) in DMSO
Solvent A 250 ml four-neck (14/20) flask was placed on a magnetic stirrer and equipped with a digital thermometer and a dry-ice condenser with the outlet connected to a nitrogen source. A pre-punctured septum was placed on the remaining neck. The reaction flask was charged with 2-Hydroxyethylmethacrylate (20.12 g/0.1546 mol), DMSO (116.85 g/1.4956 mol), potassium carbonate (21.84 g/0.1580 mol) and benzoquinone (0.06/5.55×10$^{-4}$ mol). The reaction mixture was stirred while CTFE (18.81 g/0.1615 mol) was added subsurface in aliquots through a septum over three hours with the temperature ranging from 17-25° C. An internal standard (α,α,α-trifluorotoluene) was added to the reaction mixture to follow the reaction by FNMR.

The reaction mixture was combined with 700 ml of water and 200 ml of methylene chloride and stirred for 15 minutes. The resulting mixture was placed in a separatory funnel where two immiscible layers formed after sitting for 15 minutes. The resulting layers were separated and the bottom organic layer was washed twice with 200 ml of water. The organic layer was separated and the solvent stripped at reduced pressure to isolate the product. The amount of crude 2-Chloro-1,1,2-trifluoroethoxy methacrylate product isolated was 33.34 g. The product had a purity of 74 wt % and a yield of 64% by FNMR based on 2-Hydroxymethacrylate starting material.

The crude material was purified by short path distillation under a vacuum of approximately 1 torr. The amount of distilled product collected was 27.02 g. The distilled product had a purity of 80 wt % and a yield of 57% by FNMR based on 2-Hydroxymethacrylate starting material.

$^{19}$F NMR (CDCl$_3$): δ −88.26 ppm (F$_A$), −88.74 ppm (F$_B$)*, (q of d of d, $^2J_{Fa-Fb}$=−141 Hz, $^3J_{Fa-H}$=3.5 Hz, $^3J_{Fb-H}$=4.7 Hz), δ −154.31 (Fe) (d of t, $^3J_{F-F}$=12 Hz, $^2J_{F-H}$=48

$^1$HNMR (CDCl$_3$): δ 1.95 ppm (d of d, 3H); δ 4.20 ppm (d of d of d, 2H); δ 4.40 (d of d of d, 2H); δ 5.60 (d of m 1H) δ 6.08 ppm (d of d of d, 1H, $^2J_{H-F}$=48, $^3J_{B-Fa}$=3.5 Hz, $^3J_{H-Fb}$=4.7 Hz); δ 6.10 ppm (d of m, 1H)

* The chemical shifts of F$_A$ and F$_B$ were calculated from the AB type quartet.

Example 3 Copolymerization of 2-Chloro-1,1,2-trifluoroethoxy Methacrylate and Methyl Methacrylate Three polymers were prepared, the following shows monomer composition:

3.1 MMA: 15 grams 3.2 MMA: 14.25 grams and 2-Chloro-1,1,2-trifluoroethoxy methacrylate: 0.75 grams 3.3 MMA: 12.00 grams and 2-Chloro-1,1,2-trifluoroethoxy methacrylate: 3.00 grams Monomers according to the above were mixed at room temperature in a glass vial. Once dispersed, about 75 ppm initiator, Luperox 11M75 (product of Arkema Inc.) were are added to the reaction mix in vials and sealed accordingly. The vial is immersed and heated in the water bath at 61° C. for 2 hours; subsequent polymerization is done by heating the vial to 120° C. for an hour. A transparent acrylic polymers were obtained.

Example 4 Molecular Weight Determination Using GPC

Waters 2695 coupled to Wyatt HELEOS II, Wyatt Viscostar III differential viscometer and Wyatt T-rEX Differential Refractometer Columns: Two PL Gel mixed C columns and a guard column (7.8 mm I.D.×30 cm, 5 μm)

Solvent: THF (HPLC grade)

Temperature: 35° C.

Flow rate: 1.0 mL/min

Injection volume: 100 μL,

Sample Concentration: ~1.0 mg/mL (Samples were not filtered)

Standards: Ten poly(methyl methacrylate) standards ranging in M$_p$ from 550 to 1,677,000 g/mol Polystyrene 30,000 g/mol was used to normalize the HELEOS II.

Analysis: ASTRA 6; Calibration data was fitted to a cubic polynomial with R$^2$ of at least 0.999.

| | Polymer | M$_n$ (g/mol) |
|---|---|---|
| Example 3.1 | PMMA control | 327,000 |
| Example 3.2 | 5 wt % 2-Chloro-1,1,2-trifluoroethoxy methacrylate | 274,000 |
| Example 3.3 | 20 wt % 2-Chloro-1,1,2-trifluoroethoxy methacrylate | 385,000 |

Example 5 Copolymerization of 2-Chloro-1,1,2-trifluoroethoxy Methacrylate and Methyl Methacrylate Three polymers were prepared, the following shows monomer composition:

5.1 MMA: 13.50 grams and 2-Chloro-1,1,2-trifluoroethoxy methacrylate: 1.50 grams 5.2 2-Chloro-1,1,2-trifluoroethoxy methacrylate: 15.00 grams Monomers according to the above were mixed at room temperature in a glass vial. Once dispersed, about 40 ppm initiator, Luperox 11M75 (product of Arkema Inc.) were are added to the reaction mix in vials and sealed accordingly. The vial is immersed and heated in the water bath at 61° C. for 2 hours; subsequent polymerization is done by heating the vial to 120° C. for an hour. A transparent acrylic polymers were obtained.

Example 6 Molecular Weight Determination Using GPC

Using the same GPC method as in Example 4, the following results were obtained,

| | Polymer | M$_n$ (g/mol) |
|---|---|---|
| Example 5.1 | 10 wt % 2-Chloro-1,1,2-trifluoroethoxy methacrylate | 999,000 |
| Example 5.2 | 100 wt % 2-Chloro-1,1,2-trifluoroethoxy methacrylate | 1,490,000 |

Example 7 Refractive Index (RI) of Resulted Polymers

Polymers in Example 4.2 and Example 2.1 were dissolved tetrahydrofuran (THF) at solid concentration of about 40 wt % of polymer. The solutions were diluted to about 16 wt % of polymer so that high quality film could be made. The films were dried so that they were free of solvent. The film sample was loaded on the sample holder of J457 Refractometer by Rudolph Research Analytical. The sample was initially heated to 50° C. for two hour to remove any residual solvent, then cooled down to 20° C. for four hours until refractive index was stable and film quality was excellent as indicated by the Refractometer, the results are summarized as the following,

| | Polymer | RI |
|---|---|---|
| Example 3.1 | PMMA control | 1.491 |
| Example 5.2 | 100 wt % 2-Chloro-1,1,2-trifluoroethoxy methacrylate | 1.453 |

The results show that poly(2-Chloro-1,1,2-trifluoroethoxy methacrylate) has RI of 1.453 which is lower than PMMA, and it is conceivable that its copolymer with MMA has RI of between 1.453 and 1.491.

What is claimed is:

1. A polymer comprising, in polymerized form, at least one haloalkyl ether (meth)acrylate corresponding to general structure (I):

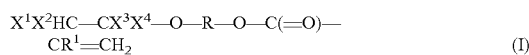

wherein R is an organic moiety, and a) $X^1$ is chlorine and $X^2$, $X^3$ and $X^4$ are fluorine or b) $X^3$ is chlorine and $X^1$, $X^2$ and $X^4$ are fluorine, and $R^1$ is hydrogen or methyl.

2. The polymer of claim 1, wherein the polymer comprises, in polymerized form, at least one haloalkyl ether (meth)acrylate corresponding to general structure (I) wherein R is an alkylene segment or a poly(oxyalkylene) segment.

3. The polymer of claim 1, wherein the polymer comprises, in polymerized form, at least one haloalkyl ether (meth)acrylate corresponding to general structure (I) wherein R is an ethylene or propylene segment or a poly(oxyethylene) or poly(oxypropylene) segment.

4. The polymer of claim 1, wherein the polymer comprises, in polymerized form, at least one haloalkyl ether (meth)acrylate corresponding to general structure (I) wherein R is $-[CH_2CH_2O]_n-CH_2CH_2-$ and n is 0 or an integer of from 1 to 10.

5. The polymer of claim 1, wherein the moiety $X^1X^2HC-CX^3X^4-O-R-O-$ has a molecular weight not greater than 900 daltons.

6. The polymer of claim 1, wherein R is a non-halogenated organic moiety.

7. The polymer of claim 1, wherein R is an aliphatic organic moiety, optionally containing one or more oxygen atoms.

8. The polymer of claim 1, wherein R is a saturated aliphatic organic moiety, optionally containing one or more ether oxygen atoms.

9. The polymer of claim 1, wherein the polymer is a copolymer of a) said at least one haloalkyl ether (meth)acrylate and b) at least one (meth)acrylate-functionalized compound other than said haloalkyl ether (meth)acrylate.

10. An article of manufacture comprising at least one haloalkyl ether (meth)acrylate in accordance with claim 1.

11. An adhesive, coating, paint, sealant, fiber, textile, molded article, films, sheet, laminate, or composite comprising at least one haloalkyl ether (meth)acrylate in accordance with claim 1.

12. A curable composition comprising a) a haloalkyl ether (meth)acrylate corresponding to general structure (I):

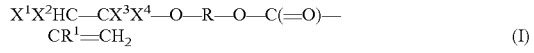
$$X^1X^2HC-CX^3X^4-O-R-O-C(=O)-CR^1=CH_2 \qquad (I)$$

wherein R is an organic moiety and a) $X^1$ is chlorine and $X^2$, $X^3$ and $X^4$ are fluorine or b) $X^3$ is chlorine and $X^1$, $X^2$ and $X^4$ are fluorine, and b) at least one of i) a (meth)acrylate-functionalized compound other than said haloalkyl ether (meth)acrylate or ii) a curing agent.

13. The curable composition of claim 12, additionally comprising at least one co-monomer which is not said haloalkyl ether (meth)acrylate.

14. A method of making a polymer, comprising polymerizing one or more monomers comprised of at least one haloalkyl ether (meth)acrylate corresponding to general structure (I):

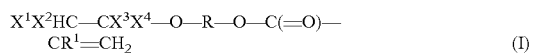
$$X^1X^2HC-CX^3X^4-O-R-O-C(=O)-CR^1=CH_2 \qquad (I)$$

wherein R is an organic moiety and a) $X^1$ is chlorine and $X^2$, $X^3$ and $X^4$ are fluorine or b) $X^3$ is chlorine and $X^1$, $X^2$ and $X^4$ are fluorine.

* * * * *